United States Patent [19]

Moyiyasu

[11] Patent Number: 5,441,748
[45] Date of Patent: Aug. 15, 1995

[54] AGENTS FOR DISTRIBUTING GALLSTONES

[75] Inventor: Akihito Moyiyasu, Sendai, Japan

[73] Assignee: Senju Pharmaceutical Co., Ltd., Osaka, Japan

[21] Appl. No.: 150,252

[22] Filed: Nov. 10, 1993

Related U.S. Application Data

[63] Continuation of Ser. No. 823,977, Jan. 23, 1992, abandoned.

[30] Foreign Application Priority Data

Jan. 26, 1991 [JP] Japan ................. 3-025596

[51] Int. Cl.$^6$ ............... A61K 33/10; A61K 31/22
[52] U.S. Cl. ............... 424/686; 514/550; 514/877
[58] Field of Search ............... 514/550, 877; 424/686

[56] References Cited

U.S. PATENT DOCUMENTS 4,451,454  5/1984  Wong ................. 424/127

FOREIGN PATENT DOCUMENTS 74426  3/1983  European Pat. Off. .
2192790  1/1988  United Kingdom .

OTHER PUBLICATIONS

Chemical Abstracts 113:46282y 1989 Ziggiotti et al.
Chemical Abstracts 112: 204679u (1990).
Chemical Abstracts 111: 534n (1989).
Cusgchieri et al—Gut 30 (12), 1989, pp. 1786–1794 (Abstract).
*Soviet Inventions Illustrated*, Section Ch: Chemical Week, D36, Oct. 14, 1981, 231, 516-789.
Wosiewitz et al., "Pigment Gallstone Dissolution in Vitro," *Scandinavian Journal of Gastroenterology*, vol. 24, 1989, pp. 373-380.
Niu et al., "Addition of N–Acetylcysteine to Aqueous Model Bile. . . ", *Gastroenterology*, vol. 98, Jan.–Jun. 1990, pp. 454–463.

*Primary Examiner*—Marianne M. Cintins
*Assistant Examiner*—K. Weddington
*Attorney, Agent, or Firm*—Merchant, Gould, Smith, Edell, Welter & Schmidt

[57] ABSTRACT

An aqueous agent for disintegrating gallstones containing an alkali metal carbonate such as sodium or potassium hydrogen carbonate and optionally N-acetylcysteine.

6 Claims, No Drawings

AGENTS FOR DISTRIBUTING GALLSTONES

This application is a continuation of U.S. application Ser. No. 07/823,977 filed Jan. 23, 1992.

BACKGROUND OF THE INVENTION

1. Field of the Invention

The present invention relates to an agent for disintegrating gallstones, and more particularly to an agent for disintegrating gallstones containing an alkali metal carbonate or a combination of an alkali metal carbonate and N-acetylcysteine as its effective components.

2. Related Arts

The statistical study shows that gallstone carriers reach about 9% of the population in Japan. In 1989, the cholecystolithiasis patients were reported to be 270,000, most of whom were subjected to surgical lithectomy. The gallstones are classified into cholesterol gallstones and pigment gallstones (bilirubin calcium and black-pigment stones) based on the component thereof. Studies on an agent for dissolving gallstones have been performed for a long time, resulting in the development of formulations of bile acid such as ursodeoxycholic acid and chenodeoxycholic acid for dissolving choresterol gallstones. Clinical tests have proved that such formulations are effective for gallstone dissolution. However, actual effect for gallstone dissolution given by such formulations depends on the size of the stone and cholecyst function, whereby the patient should be dosed for a long period such as a half- year to a year or more. A suitable agent for dissolving pigment stones has not yet been developed in spite of various studies.

The inventor has found out from studies on composition of the gallstones that mucopolysaccharides and mucoproteins (hereinafter abbreviated to muco-substances) play an important role as a component for binding the crystalline cholesterol or bilirubin. On the other hand, SH-compounds including N-acetylcysteine have been known to have action for splitting off the S—S bond of muco-substances. In particular, it has been reported that N-acetylcysteine accelerates dissolution of cholesterol gallstones [see Scand. J. Gastroent., 24, 373–380 (1989); Gastroenterology., 98, 454–463 (1990)]. However, this document reports that the dissolution of cholesterol gallstones takes about 10 hours to several weeks, and further that the absolute effect is small.

On the other hand, the effective action of alkali metal carbonates for disintegrating gallstones has not been known.

Under such circumstance, it is desired to develop an agent which can easily destroy gallstones to make their small pieces which can be removed without surgical lithectomy.

SUMMARY OF THE INVENTION

The invention provides an aqueous solution comprising an alkali metal carbonate or its combination with N-acetyl-cysteine.

DESCRIPTION OF THE PREFERRED EMBODIMENT

Examples of the alkali metal carbonates include sodium hydrogen carbonate, potassium hydrogen carbonate, sodium carbonate, potassium carbonate or the like, among which monoalkali metal carbonate is preferable, and especially sodium hydrogen carbonate is more preferable. Preferably, the concentration of the alkali metal carbonate in the aqueous solution is 1 to 30% (W/V) (represented by weight per volume hereinafter), more preferably 5 to 20%, for example, 8%, 10% or 12%.

Suitably, N-acetylcysteine is contained in the aqueous solution at the concentration of 5 to 30%, preferably 10 to 25%, for example, 10%, 15% or 20%.

Suitable medium for the aqueous solution is distilled water, particularly sterile water.

The aqueous solution as the agent for disintegrating gallstones of the present invention is observed to have pH 7 to 10, preferably 7.5 to 9. The aqueous solution may be adjusted by adding an acid or an alkali when it does not exhibit the above mentioned pH range with only effective components.

The dose of the agent for disintegrating gallstones according to the present invention varies with the age of patient, level of disease or the like, but generally 1 to 100 ml per one time for an adult. The administration methods include the following: a method in which the agent is infused or perfused into a bile duct or gallbladder through a tube which is left at the surgery; a method in which the agent is infused into a bile duct through a T-tube inserted into the bile duct at choledocholithotomy; or a method in which the agent is retrogressively infused into a gallbladder or bile duct from duodenal mamilla part under endoscopy.

N-Acetylcysteine used for the present invention exhibits remarkably high safety, since it is clinically used for human being as an agent for protecting liver or an expectorant. The sodium hydrogen carbonate, which is representative of the alkali metal carbonate, is clinically employed as ulcer-preventive agent. Accordingly, the agent for disintegrating gallstones of the present invention exhibits high safety.

The present invention will be specifically explained hereinafter with reference to the Experiments and Examples. The percentage hereinbelow represents W/V %.

Experiment 1

Action for Disintegrating Gallstones

Gallstones (54.9 ±6.8 mg) nearest in shape, material and size were obtained from a single patient for this Experiment. The obtained gallstones were black-pigment stones having a rough structure and containing a number of muco-substances. 20% of N-acetylcysteine were respectively added to distilled water and 10% sodium hydrogen carbonate to obtain respective test solutions 1 and 2. On the other hand, a test solution 3 containing only 10% sodium hydrogen carbonate and a test solution 4 (control) containing only distilled water were prepared. One stone of the obtained gallstones was put into each test solution for observing the number of a piece of the stones by taking pictures thereof every five minutes. Table 1 shows the degree of the gallstone disintegration.

TABLE 1

| Test Solution | Number of Pieces of Stones with Time | | | | | | | | |
|---|---|---|---|---|---|---|---|---|---|
| | 0 | 5 | 10 | 15 | 20 | 25 | 30 | 35 | 40 (min.) |
| 1 | 1 | 1 | 14 | 24 | 47 | 113 | 129 | 143 | 174 |
| 2 | 1 | 1 | 13 | 52 | 256 | 332 | 389 | 423 | 450 |
| 3 | 1 | 41 | 58 | 123 | 180 | 185 | 203 | 230 | 315 |
| 4 | 1 | 1 | 1 | 1 | 1 | 1 | 1 | 1 | 1 |

As is apparent from Table 1, gallstone disintegration was observed in test solutions 1 to 3 except for distilled water (control test solution 4). In particular, gallstone disintegration was remarkably observed in the test solution 2 in which N-acetylcysteine was added to 10% sodium hydrogen carbonate compared to the test solutions 1 and 3.

Experiment 2

Under the same conditions as in the Experiment 1, gallstone disintegration was observed using a test solution 5 containing 10% potassium hydrogen carbonate and a control test solution 6 containing 10% sodium hydroxide. The results were shown in Table 2.

TABLE 2

| Test Solution | Number of Pieces of Stones with Time | | | | | | | |
|---|---|---|---|---|---|---|---|---|
| | 5 | 10 | 15 | 20 | 25 | 30 | 35 | 40 (min.) |
| 5 | 22 | 43 | 68 | 84 | 103 | 112 | 126 | 166 |
| 6 | 1 | 1 | 1 | 1 | 4 | 8 | 11 | 15 |

Gallstone disintegration was rarely observed in the control test solution 6.

Experiment 3

Under the same conditions as in the Experiment 1, the Experiment 3 was performed using a test solution 7 in which 20% of N-acetylcysteine was added to 10% sodium hydrogen carbonate (pH 7.5) and a control test solution 8 in which 20% N-acetylcysteine was added to 10% potassium hydrogen carbonate (pH 7.5) for observing the difference caused by the kind of the alkali metal hydrogen carbonate. The results were shown in Table 3.

TABLE 3

| Test Solution | Number of Pieces of Stones with Time | | | | | | | |
|---|---|---|---|---|---|---|---|---|
| | 5 | 10 | 15 | 20 | 25 | 30 | 35 | 40 (min.) |
| 7 | 6 | 36 | 49 | 88 | 137 | 425 | 465 | 480 |
| 8 | 14 | 96 | 140 | 268 | 280 | 315 | 340 | 390 |

Experiment 4

Under the same conditions as in the Experiment 1, gallstone disintegration was observed using test solutions 9 to 11 in which 10% sodium hydrogen carbonate was added to 20% N-acetylcysteine solution to find out the effect of pH on gallstone disintegration. Each of the test solutions 9 to 11 varies in pH. Specifically, the test solution 9 is pH 6.0, the test solution 10 is pH 7.5 and the test solution 11 is pH 8.2. The results were shown in Table 4.

TABLE 4

| Test Solution | Number of Pieces of Stones with Time | | | | | | | |
|---|---|---|---|---|---|---|---|---|
| | 5 | 10 | 15 | 20 | 25 | 30 | 35 | 40 (min.) |
| 9 (pH 6.0) | 1 | 2 | 4 | 8 | 14 | 16 | 16 | 48 |
| 10 (pH 7.5) | 6 | 36 | 49 | 88 | 137 | 425 | 465 | 480 |
| 11 (pH 8.2) | 120 | 138 | 169 | 286 | 306 | 328 | 415 | 488 |

The function of gallstone disintegration was remarkably reduced in the solution of at least pH 6.0 compared to the other solutions of different pH but of the same effective components.

Experiment 5

Under the same conditions as in the Experiment 1, gallstone disintegration was observed using test solutions 12, 13 and 3 of 1%, 5% and 10% sodium hydrogen carbonate respectively to find out the effect of concentration of the sodium hydrogen carbonate. The results were shown in Table 5.

TABLE 5

| Test Solution | Number of Pieces of Stones with Time | | | | | | | |
|---|---|---|---|---|---|---|---|---|
| | 5 | 10 | 15 | 20 | 25 | 30 | 35 | 40 (min.) |
| 12 | 1 | 5 | 11 | 16 | 18 | 28 | 35 | 38 |
| 13 | 25 | 50 | 58 | 63 | 73 | 89 | 136 | 145 |
| 3 | 41 | 58 | 123 | 180 | 185 | 203 | 230 | 315 |

The effects on gallstone disintegration were great in the cases of 5% and 10% sodium hydrogen carbonate, particularly 10% sodium hydrogen carbonate.

EXAMPLE 1

Injection for local administration was prepared by mixing the following compositions in accordance with a known method.

| | |
|---|---|
| N-Acetylcysteine | 200.0 mg |
| Sodium hydrogen carbonate | 100.0 mg |
| Distilled water | |
| Total | 300.0 mg |
| | (per 1 ml) |

The effective components of an agent according to the present invention possess action for rapidly disintegrating gallstones, thereby useful for therapy of cholecystitis.

What is claimed is:

1. A composition of matter for disintegrating gallstones consisting essentially of an aqueous solution comprising (a) a quantity of water, (b) from approximately 5 to approximately 20 weight percent, based on the quantity of water, of a sodium hydrogen carbonate and (c) from approximately 10 to approximately 25 weight percent, based on the quantity of water, of N-acetylcysteine, wherein the aqueous solution has a pH value of from approximately 7.0 to approximately 10.0.

2. The composition of claim 1 wherein the sodium hydrogen carbonate is present in an amount of from approximately 8 to approximately 12 weight percent, based on the quantity of water.

3. The composition of claim 1 wherein the N-acetylcysteine is present in an amount of from approximately 10 to approximately 20 weight percent, based on the quantity of water.

4. The composition of claim 1 wherein the aqueous solution has a pH value of from approximately 7.5 to approximately 9.0.

5. The composition of claim 1 wherein the quantity of water is a quantity of distilled water.

6. A method of treating cholecystolithiasis which comprises administering an effective amount of a composition to a patient carrying a gallstone wherein the composition administered is an aqueous solution which comprises (a) a quantity of water, (b) from approximately 5 to approximately 20 weight percent, based on the quantity of water, of sodium hydrogen carbonate and (c) from approximately 10 to approximately 25 weight percent, based on the quantity of water, of N-acetylcysteine, wherein the aqueous solution has a pH value of from approximately 7.0 to approximately 10.0.

* * * * *